(12) United States Patent
Barrett et al.

(10) Patent No.: US 10,433,884 B2
(45) Date of Patent: *Oct. 8, 2019

(54) REDUCTION INSTRUMENT, SURGICAL ASSEMBLY INCLUDING A REDUCTION INSTRUMENT AND RELATED METHOD

(71) Applicant: Zimmer Biomet Spine, Inc., Westminster, CO (US)

(72) Inventors: John Christian Barrett, West Orange, NJ (US); Michal Zentko, Cherry Hill, NJ (US); David Barry, Teaneck, NJ (US); Matthew Tobias Jacobs, Morristown, NJ (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 84 days.

This patent is subject to a terminal disclaimer.

(21) Appl. No.: 15/465,927

(22) Filed: Mar. 22, 2017

(65) Prior Publication Data

US 2017/0189083 A1   Jul. 6, 2017

Related U.S. Application Data

(63) Continuation of application No. 13/834,364, filed on Mar. 15, 2013, now Pat. No. 9,668,789.

(51) Int. Cl.
*A61B 17/70* (2006.01)

(52) U.S. Cl.
CPC ........ *A61B 17/7086* (2013.01); *A61B 17/708* (2013.01); *A61B 17/7085* (2013.01); *A61B 17/7091* (2013.01); *A61B 17/7077* (2013.01); *A61B 17/7083* (2013.01)

(58) Field of Classification Search
CPC .............. A61B 17/7077; A61B 17/708; A61B 17/7091; A61B 17/7086
See application file for complete search history.

(56) References Cited

U.S. PATENT DOCUMENTS

| 5,102,412 A | 4/1992 | Rogozinski |
|---|---|---|
| 5,112,332 A | 5/1992 | Cozad et al. |
| 5,116,334 A | 5/1992 | Cozad et al. |
| 5,181,917 A | 1/1993 | Rogozinski |

(Continued)

FOREIGN PATENT DOCUMENTS

| CN | 1913836 A | 2/2007 |
|---|---|---|
| CN | 104042316 A | 9/2014 |

OTHER PUBLICATIONS

"Chinese Application Serial No. 2014100975302, Response filed May 21, 2018 to Office Action dated Mar. 5, 2018", (W/ English Translation of Claims), 10 pgs.

(Continued)

*Primary Examiner* — Ellen C Hammond
(74) *Attorney, Agent, or Firm* — Schwegman Lundberg & Woessner, P.A.

(57) ABSTRACT

A surgical instrument for reducing a rod into a saddle of a fixation member includes a distal end for engaging the saddle and a proximal end. A reducing device is disposed between the distal end and the proximal end. The reducing device is operative to reduce the rod into the saddle. The reducing device defines a throughbore. The throughbore provides access there through by a first drive member to secure a plug to the saddle.

20 Claims, 11 Drawing Sheets

(56) References Cited

U.S. PATENT DOCUMENTS

| | | | |
|---|---|---|---|
| 5,281,223 | A | 1/1994 | Ray |
| 5,306,275 | A | 4/1994 | Bryan |
| 5,498,262 | A | 3/1996 | Bryan |
| 5,545,166 | A | 8/1996 | Howland |
| 5,630,816 | A | 5/1997 | Kambin |
| 5,676,665 | A | 10/1997 | Bryan |
| 5,704,937 | A | 1/1998 | Martin |
| 5,772,661 | A | 6/1998 | Michelson |
| 5,810,817 | A | 9/1998 | Roussouly et al. |
| 5,928,232 | A | 7/1999 | Howland et al. |
| 5,947,965 | A | 9/1999 | Bryan |
| 6,015,409 | A | 1/2000 | Jackson |
| 6,090,113 | A | 7/2000 | Le Couedic et al. |
| 6,267,765 | B1 | 7/2001 | Taylor |
| 6,375,657 | B1 | 4/2002 | Doubler et al. |
| 6,440,132 | B1 | 8/2002 | Jackson |
| 6,458,131 | B1 | 10/2002 | Ray |
| 6,558,390 | B2 | 5/2003 | Cragg |
| 6,652,526 | B1 | 11/2003 | Arafiles |
| 6,743,231 | B1 | 6/2004 | Gray et al. |
| 6,749,614 | B2 | 6/2004 | Teitelbaum et al. |
| 6,802,844 | B2 | 10/2004 | Ferree |
| 6,821,277 | B2 | 11/2004 | Teitelbaum |
| 6,827,719 | B2 | 12/2004 | Ralph et al. |
| 7,651,502 | B2 | 1/2010 | Jackson |
| 7,670,358 | B2 | 3/2010 | Barry |
| 7,776,072 | B2 | 8/2010 | Barry |
| D649,243 | S | 11/2011 | Barry et al. |
| 8,197,519 | B2 | 6/2012 | Schlaepfer et al. |
| 8,308,774 | B2 | 11/2012 | Hoffman et al. |
| 8,361,121 | B2 | 1/2013 | Barry |
| 8,512,383 | B2 | 8/2013 | Mclean |
| 8,545,505 | B2 | 10/2013 | Sandstrom et al. |
| 8,603,094 | B2 | 12/2013 | Walker et al. |
| 8,672,944 | B2 | 3/2014 | Boachie-Adjei et al. |
| 8,951,257 | B2 | 2/2015 | Lenke et al. |
| 9,050,143 | B2 | 6/2015 | May et al. |
| 9,138,261 | B2 | 9/2015 | Di Lauro et al. |
| 9,155,573 | B2 | 10/2015 | May et al. |
| 9,668,789 | B2 | 6/2017 | Barrett et al. |
| 2005/0149036 | A1 | 7/2005 | Varieur et al. |
| 2005/0149053 | A1 | 7/2005 | Varieur et al. |
| 2005/0245928 | A1 | 11/2005 | Colleran et al. |
| 2006/0036254 | A1 | 2/2006 | Lim |
| 2006/0074418 | A1 | 4/2006 | Jackson |
| 2006/0079909 | A1 | 4/2006 | Runco et al. |
| 2006/0111712 | A1 | 5/2006 | Jackson |
| 2006/0149236 | A1 | 7/2006 | Barry |
| 2007/0078460 | A1 | 4/2007 | Frigg et al. |
| 2007/0213716 | A1 | 9/2007 | Lenke et al. |
| 2008/0015601 | A1 | 1/2008 | Castro et al. |
| 2008/0045956 | A1 | 2/2008 | Songer et al. |
| 2008/0319477 | A1 | 12/2008 | Justis et al. |
| 2009/0018593 | A1 | 1/2009 | Barrus et al. |
| 2009/0157125 | A1 | 6/2009 | Hoffman et al. |
| 2009/0228053 | A1 | 9/2009 | Kolb et al. |
| 2010/0262198 | A1 | 10/2010 | Braunschweiler et al. |
| 2011/0087298 | A1 | 4/2011 | Jones |
| 2011/0093022 | A1 | 4/2011 | Runco et al. |
| 2011/0118791 | A1 | 5/2011 | Nunley et al. |
| 2011/0125192 | A1 | 5/2011 | Justis et al. |
| 2011/0166606 | A1 | 7/2011 | Stihl et al. |
| 2011/0172714 | A1 | 7/2011 | Boachie-adjei et al. |
| 2011/0257692 | A1 | 10/2011 | Sandstrom et al. |
| 2011/0263945 | A1 | 10/2011 | Peterson et al. |
| 2011/0313477 | A1 | 12/2011 | Mclean et al. |
| 2012/0035668 | A1 | 2/2012 | Manninen et al. |
| 2012/0191144 | A1* | 7/2012 | Peultier .............. A61B 17/7086 606/86 A |
| 2012/0203279 | A1 | 8/2012 | Walters et al. |
| 2012/0215266 | A1 | 8/2012 | Jones |
| 2012/0277800 | A1 | 11/2012 | Jackson |
| 2013/0018419 | A1 | 1/2013 | Rezach et al. |
| 2013/0046345 | A1 | 2/2013 | Jones et al. |
| 2013/0072983 | A1 | 3/2013 | Lindquist et al. |
| 2013/0096624 | A1* | 4/2013 | Di Lauro ........... A61B 17/7011 606/279 |
| 2013/0211453 | A1 | 8/2013 | Lenke et al. |
| 2013/0317558 | A1 | 11/2013 | Varieur et al. |
| 2013/0331892 | A1 | 12/2013 | Peterson et al. |
| 2014/0046372 | A1 | 2/2014 | Ibrahim et al. |
| 2014/0052187 | A1 | 2/2014 | McBride et al. |
| 2014/0114354 | A1 | 4/2014 | May et al. |
| 2014/0148865 | A1 | 5/2014 | Hennard et al. |
| 2014/0163617 | A1 | 6/2014 | Boachie-adjei et al. |
| 2014/0163625 | A1 | 6/2014 | Meyer et al. |
| 2014/0194939 | A1 | 7/2014 | Seelig |
| 2014/0277145 | A1 | 9/2014 | Reitblat et al. |
| 2014/0277170 | A1 | 9/2014 | Barrett et al. |
| 2014/0277197 | A1 | 9/2014 | Brown et al. |
| 2014/0364912 | A1 | 12/2014 | May et al. |
| 2015/0335359 | A1 | 11/2015 | May et al. |

OTHER PUBLICATIONS

U.S. Appl. No. 13/834,364, filed Mar. 15, 2013, Reduction Instrument, Surgical Assembly Including a Reduction Instrument and Related Method.
"Chinese Application Serial No. 2014100975302, Office Action dated Mar. 5, 2018", w. English Claims, 9 pgs.
"Chinese Application Serial No. 2014100975302, Response filed Jul. 12, 2017 to Office Action dated Mar. 1, 2017", w/ English Translation, 17 pgs.
"U.S. Appl. No. 13/834,364, Advisory Action dated Nov. 4, 2015", 6 pgs.
"U.S. Appl. No. 13/834,364, Examiner Interview Summary dated Oct. 15, 2015", 3 pgs.
"U.S. Appl. No. 13/834,364, Final Office Action dated Aug. 19, 2016", 10 pgs.
"U.S. Appl. No. 13/834,364, Final Office Action dated Sep. 3, 2015", 15 pgs.
"U.S. Appl. No. 13/834,364, Non Final Office Action dated Feb. 22, 2016", 9 pgs.
"U.S. Appl. No. 13/834,364, Non Final Office Action dated Mar. 3, 2015", 14 pgs.
"U.S. Appl. No. 13/834,364, Notice of Allowance dated Jan. 31, 2017", 5 pgs.
"U.S. Appl. No. 13/834,364, Response filed Feb. 11, 2014 to Restriction Requirement dated Dec. 11, 2014", 7 pgs.
"U.S. Appl. No. 13/834,364, Response filed Jul. 6, 2015 to Non Final Office Action dated Mar. 3, 2015", 12 pgs.
"U.S. Appl. No. 13/834,364, Response filed Jul. 22, 2016 to Non Final Office Action dated Feb. 22, 2016", 9 pgs.
"U.S. Appl. No. 13/834,364, Response filed Oct. 15, 2015 to Final Office Action dated Sep. 3, 2015", 10 pgs.
"U.S. Appl. No. 13/834,364, Response filed Nov. 18, 2016 to Final Office Action dated Aug. 19, 2016", 10 pgs.
"U.S. Appl. No. 13/834,364, Response filed Dec. 3, 2015 to Advisory Action dated Nov. 4, 2015", 10 pgs.
"U.S. Appl. No. 13/834,364, Restriction Requirement dated Dec. 11, 2014", 7 pgs.
"Chinese Application Serial No. 2014100975302, Office Action dated Mar. 1, 2017", 7 pgs.
"European Application Serial No. 14159701.3, Extended European Search Report dated Jul. 3, 2014", 9 pgs.
"European Application Serial No. 14159701.3, Response filed Dec. 16, 2014 to Extended European Search Report dated Jul. 3, 2014", 11 pgs.
"European Application Serial No. 204794, Extended European Search Report dated Jul. 3, 2014".
Richard, P, et al., "Biomechanics of spinal deformity", Abstract only, Neurosurg Focus 14, (2003).
U.S. Appl. No. 13/834,364, U.S. Pat. No. 9,668,789, filed Mar. 15, 2013, Reduction Instrument, Surgical Assembly Including a Reduction Instrument and Related Method.

\* cited by examiner

REDUCTION INSTRUMENT, SURGICAL ASSEMBLY INCLUDING A REDUCTION INSTRUMENT AND RELATED METHOD

PRIORITY APPLICATIONS

This application is a continuation of U.S. patent application Ser. No. 13/834,364, filed Mar. 15, 2013, the contents of which is incorporated herein by reference in its entirety.

FIELD OF THE INVENTION

The present teachings generally relate to orthopedic instruments. More particularly, the present teachings relate to a reduction instrument and a surgical assembly including a reduction instrument. The present teachings also more particularly relate to a method.

BACKGROUND

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue or correct the deformity, which can require the use of one or more orthopedic prosthesis, such as orthopedic nails, screws, implants, etc.

In one example, in order to restore function to or correct a deformity of the spinal column, one or more implants can be coupled to each vertebral body and interconnected via a suitable device. In one example, implants or anchors can be coupled to each vertebral body, and a connecting device, such as a rod, can be coupled to each of the anchors to stabilize or fix the vertebral bodies relative to each other. Generally, multiple anchors can be attached to each vertebral body so that multiple rods can be used to stabilize the spinal column. In one example, one or more reduction instruments and rotation instruments can cooperate with the multiple anchors to restore function to or correct a deformity of the spinal column.

SUMMARY

The present teachings relate to instruments for use in restoring function or correcting a deformity, and more specifically relate to a combination reduction and rotation instrument for restoring function to or correcting a deformity of the spinal column.

In accordance with one particular aspect, the present teachings provide a surgical instrument for reducing a rod into a saddle of a fixation member. The surgical instrument includes a distal end for engaging the saddle and a proximal end. A reducing mechanism is disposed between the distal end and the proximal end. The reducing mechanism is operative to reduce the rod into the saddle. The reducing mechanism defines a throughbore. The throughbore provides access there through by a first drive member to secure a plug to the saddle.

In accordance with another particular aspect, the present teachings provide a surgical assembly including a rotation instrument and a reduction instrument. The reduction instrument is operative for reducing a rod into a saddle of a fixation member and includes a reducing mechanism defining a throughbore. The throughbore provides access there through by a first drive member to secure a plug to the saddle.

In accordance with yet another particular aspect, the present teachings relate to a surgical method. The surgical method includes engaging a bone with a bone engaging member. The bone engaging member includes a saddle for receiving a rod. The method additionally includes providing a surgical assembly including a reduction instrument having a drive mechanism for reducing the rod relative into the saddle and engaging the saddle of the bone engaging member with the surgical assembly. The method further includes engaging a plug to the saddle to secure the rod to the bone engaging member by passing a first drive member through a throughbore of the drive mechanism.

DRAWINGS

The drawings described herein are for illustration purposes only and are not intended to limit the scope of the present teachings in any way.

DESCRIPTION OF VARIOUS ASPECTS

Figure 1:
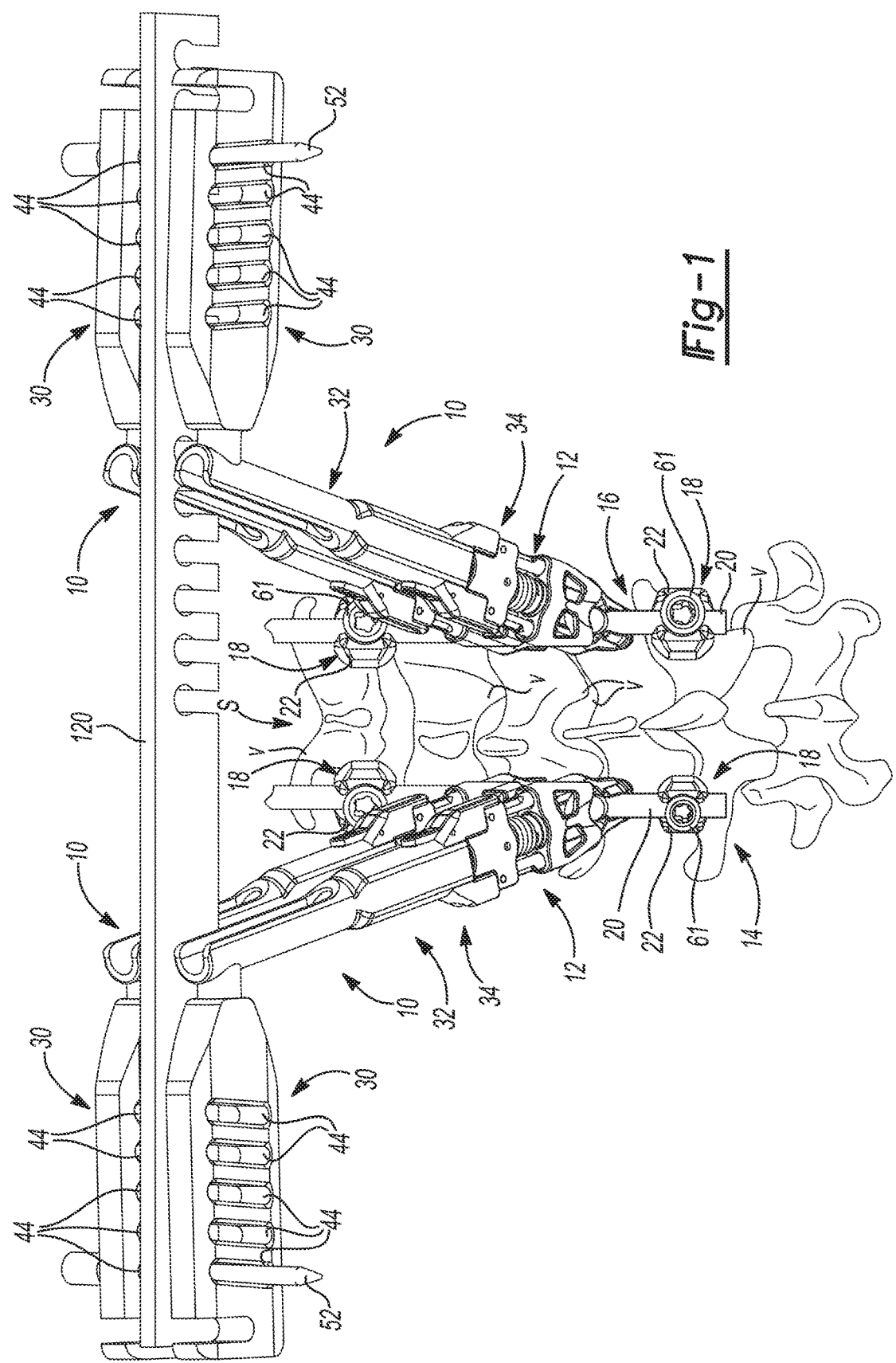
FIG. 1 is an environmental illustration of an assembly including an exemplary rotation instrument coupled to a rod reduction instrument for use in a surgical procedure according to the present teachings.

The following description is merely exemplary in nature and is not intended to limit the present teachings, application, or uses. It should be understood that throughout the drawings, corresponding reference numerals indicate like or corresponding parts and features. Although the following description is related generally to a combination reduction and rotation instrument for use in restoring function to or correcting a deformity of the spinal column, such as in the case of an axial, coronal or sagittal deformity of the spinal column, it will be understood that the system as described and claimed herein can be used in any appropriate surgical procedure, such as in a minimally invasive orthopedic alignment or fixation procedure. Therefore, it will be understood that the following discussions are not intended to limit the scope of the present teachings and claims herein.

With reference to FIGS. 1-6, a rotation instrument 10 is shown. The rotation instrument 10 may be particularly adapted for spinal fixation procedures. Various aspects of the present teachings, however, may have application for other procedures. In certain applications, one or more rotation instruments 10 can be used to correct a deformity of a spinal column S. In one example, with reference to FIG. 1, a rotation instrument 10 can cooperate with a rod reduction instrument 12, a first spinal fixation system 14 and a second spinal fixation system 16 to correct a deformity of the spinal column S.

In this example, the first fixation system 14 and the second fixation system 16 can be coupled to the spinal column S along both sides of the spinal column S such that the first fixation system 14 can be generally parallel to the second fixation system 16. It should be noted, however, that one of the first fixation system 14 and second fixation system 16 could be coupled to the spinal column 5, if desired. Further, it should be noted that the first fixation system 14 and second fixation system 16 could be coupled so as to extend along a single side of the spinal column S. Each of the first fixation system 14 and the second fixation system 16 can include one or more bone engaging members 18, which can be interconnected via an elongated member or connecting rod 20. It should be noted that although the first fixation system 14 and second fixation system 16 are illustrated and described herein as being used with the connecting rod 20, the first fixation system 14 and second fixation system 16 need not be connected via the connecting rod 20. In addition, it should be noted that the rotation instrument 10 can be used during a surgical procedure prior to the connecting rod 20 being coupled to the first fixation system 14 and second fixation system 16, if the connecting rod 20 is employed with the first fixation system 14 and second fixation system 16. Further, although the first fixation system 14 and the second fixation system 16 are illustrated herein as spanning multiple levels of the spinal column 5, the first fixation system 14 and the second fixation system 16 could be used in a single level spinal fixation procedure, if desired.

In this regard, in a single level spinal fixation procedure, two bone engaging members 18 can receive a single connecting rod 20. A multiple level spinal fixation procedure, however, will generally require additional bone engaging members 18, as illustrated. In addition, the bone engaging members 18 need not be coupled to adjacent vertebral bodies V as illustrated, but rather, the bone engaging members 18 can be positioned so as to skip adjacent vertebral bodies V, if desired.

The bone engaging members 18 can comprise any suitable device that is capable of coupling to a portion of the vertebral body V, such as a spinal hook or bone anchor. The connecting rod 20 can comprise any suitable device capable of interconnecting the bone engaging members 18. For example, the first fixation system 14 and second fixation system 16 can be composed of spinal hooks, bone anchors and connecting rods, which are commercially available from Biomet, Inc. of Warsaw, Ind. In one example, the first fixation system 14 and the second fixation system 16 can comprise bone engaging members 18 and connecting rod(s) 20 selected from one or more of the POLARIS™ Deformity System, POLARIS™ 5.5 or 6.35 Spinal System, or ARRAY® Spinal System, each of which are commercially available from Biomet, Inc. of Warsaw, Ind.

In addition to or in the alternative, the bone engaging members 18 can comprise those disclosed in commonly owned U.S. patent application Ser. No. 12/614,734, filed on Nov. 9, 2009 and entitled "Multiplanar Bone Anchor System," and/or those disclosed in commonly owned U.S. patent application Ser. No. 13/103,069, filed on May 8, 2011 and entitled "Multiplanar Bone Anchor System," each of which are incorporated herein by reference. The bone engaging members 18 could also comprise one or more of the bone anchors disclosed in commonly owned U.S. patent application Ser. No. 12/688,013, filed on Jan. 15, 2010 and/or commonly owned U.S. patent application Ser. No. 12/842,556, filed on Jul. 23, 2010, each entitled "Uniplanar Bone Anchor" and each incorporated herein by reference.

As the bone engaging members 18 and connecting rod(s) 20 can be generally known, the bone engaging members 18 and connecting rod(s) 20 will not be discussed in great detail herein. Briefly, however, the bone engaging members 18 can include a connecting portion or saddle 22, which can be used to couple the rod reduction instrument 12 to the bone engaging members 18.

With continued reference to FIG. 1, the rod reduction instrument 12 can be coupled to the bone engaging members 18 and can be used to reduce the connecting rod 20 into the bone engaging members 18. The rod reduction instrument 12 can comprise any suitable device capable of reducing the connecting rod 20 into the bone engaging members 18. For example, the rod reduction instrument 12 can be commercially available from Biomet, Inc. of Warsaw, Ind. In one example, the rod reduction instrument 12 can be selected from the ROCKET™ Instrumentation system commercially available from Biomet, Inc. of Warsaw, Ind. In addition to or in the alternative, a suitable rod reduction instrument 12 can comprise that disclosed in commonly owned U.S. patent application Ser. No. 29/391,226, filed on May 5, 2011, entitled "Pusher For A Rod Reduction Device" and incorporated by reference herein.

Figure 2:
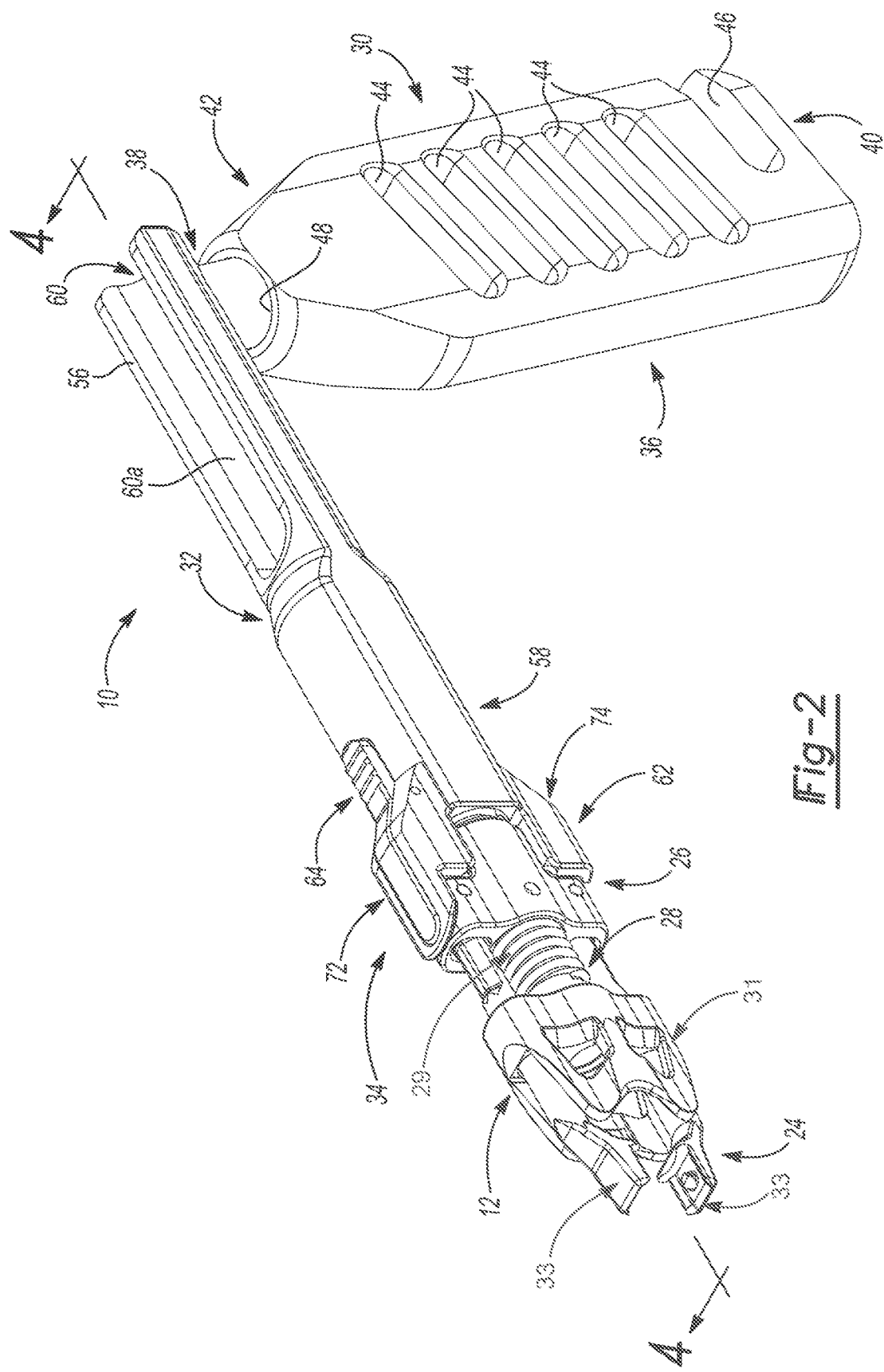
FIG. 2 is a perspective illustration of the exemplary rotation instrument coupled to the rod reduction instrument of FIG. 1.

With reference to FIG. 2, the rod reduction instrument 12 in the embodiment illustrated may include a distal end 24, a proximal end 26 and a reducing mechanism 28. The distal end 24 can be shaped and configured to be coupled to the bone engaging member 18. The proximal end 26 can be coupled to the rotation instrument 10, as will be discussed in greater detail herein. The reducing mechanism 28 can be disposed between the distal end 24 and the proximal end 26. In a conventional manner, the reducing device or mechanism 28 can move the distal end 24 relative to the proximal end 26 to reduce the connecting rod 20 onto the bone engaging member 18.

With reference to FIG. 1, the rotation instrument 10 can be coupled to the rod reduction instrument 12 to enable the creation of a moment arm to rotate at least one vertebral body V around an axis substantially parallel to the final orientation of the connecting rod 20, if employed, to correct the deformity of the spinal column S. The coupling of the rotation instrument 10 directly to the rod reduction instrument 12 can reduce or eliminate steps during an exemplary surgical procedure as the surgeon does not need to remove the rod reduction instrument 12 to rotate the vertebral body V. The rotation instrument 10 can include a graspable portion or handle 30, a rotation tube 32 and an attachment system 34.

Figure 3:
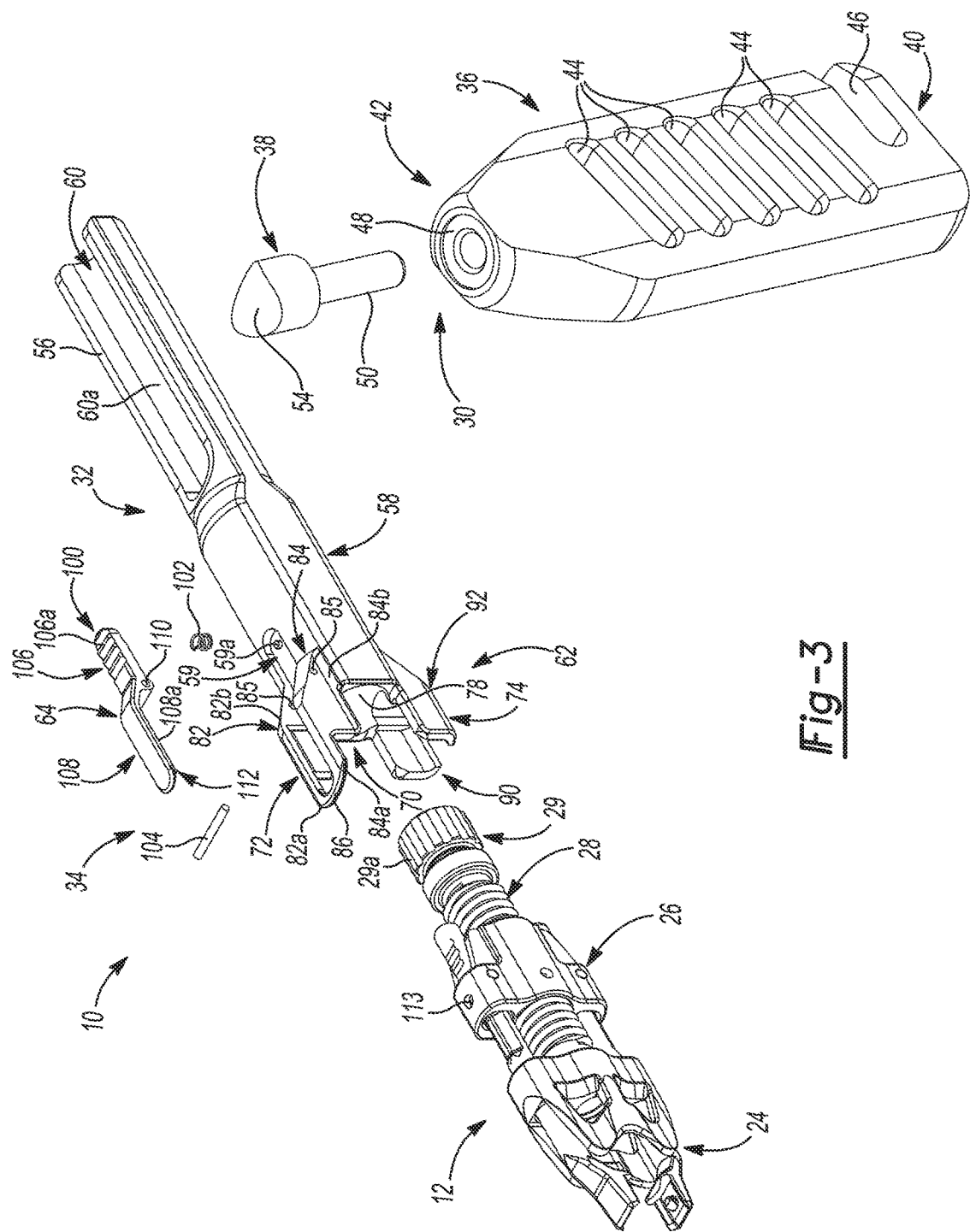
FIG. 3 is a partially exploded view of the assembly of the rotation instrument and rod reduction instrument of FIG. 2.

With regard to FIGS. 2 and 3, the handle 30 can enable the application of a force to the rotation instrument 10. The handle 30 can include a body 36 and a coupling post 38. It should be noted that although the handle 30 is illustrated and described herein as comprising the body 36 and the coupling post 38, the handle 30 could be integrally formed. In addition, although the handle 30 is described herein as being separate and discrete from the rotation tube 32 and attachment system 34, the handle 30 could be integrally formed with the rotation tube 32 and attachment system 34, if desired. Further, although the handle 30 is illustrated herein as being coupled to the rotation tube 32 along an axis that intersects a longitudinal axis of the rotation tube 32, the handle 30 could be coupled along an axis that is substantially parallel to or the same as the longitudinal axis of the rotation tube 30. The handle 30 can be composed of a suitable biocompatible material, such as a biocompatible metal, metal alloy or polymer. In addition, the body 36 and the coupling post 38 can be composed of the same or different materials. For example, the body 36 can be composed of a biocompatible polymer and the coupling post 38 can be composed of a biocompatible metal.

The body 36 can have a proximal or first end 40, a distal or second end 42 and a plurality of coupling apertures or slots 44. The first end 40 can include a U-shaped aperture 46, which can enable the surgeon to manipulate the rotation instrument 10. In one example, a loop of material can be hung through the U-shaped aperture 46 of the handle 30 to enable manipulation of the rotation instrument 10. In one example, a loop of gauze can be hung through the U-shaped aperture 46 to enable the surgeon to manipulate the rotation instrument 10 with his/her foot. In instances where multiple rotation instruments, such as rotation instruments 10, are coupled together to operate en bloc, the loop of gauze can enable the surgeon to manipulate the coupled instruments substantially simultaneously. The second end 42 of the body 36 can include a bore 48. The bore 48 can receive a proximal end 50 of the coupling post 38 to couple the body 36 to the coupling post 38, as will be discussed further herein.

The slots 44 can be generally elongated, and can be formed along the body 36 from the first end 40 to the second end 42. It should be noted that although the slots 44 are illustrated as elongated substantially elliptical slots, the slots 44 could have any desired shape, such as rectangular, and could be positioned in any desired orientation. Further, although multiple slots 44 are described and illustrated herein, the handle 30 could include a single slot 44, if desired. The slots 44 can receive a device, such as a pin 52 (FIG. 1), to couple the rotation instrument 10 to other rotation instruments. Suitable rotation instruments include those described herein, and those commercially available from Biomet, Inc. of Warsaw, Ind., such as the Trivium™ Derotation System. In addition, suitable rotation instruments can include those described in U.S. Pat. No. 7,776,072, filed on Aug. 10, 2005, titled "System and Method for Aligning Vertebrae in the Amelioration of Aberrant Spinal Column Deviation Conditions," and incorporated herein by reference. By coupling the rotation instrument 10 to one or more adjacent rotation instruments, multiple vertebral bodies V can be rotated substantially simultaneously to enable correction over multiple levels. In addition, the slots 44 can also enable the pin 52 to be received after the deformity of the spinal column S has been corrected to temporarily hold the alignment of the spinal column S.

With continued reference to FIG. 3, the coupling post 38 can include the proximal end 50 and a distal end 54. The coupling post 38 can couple the body 36 of the handle 30 to the rotation tube 32. In one example, the proximal end 50 of the coupling post 38 can be heated and press-fit into the bore 48 so that the body 36 melts about the coupling post 38 to secure the body 36 to the coupling post 38. It should be noted that other methods and techniques could be employed to couple the coupling post 38 to the body 36, such as welding, mechanical fasteners, adhesives, etc. The distal end 54 of the coupling post 38 can be coupled to the rotation tube 32. In this regard, the distal end 54 can include a slight concavity to facilitate the placement of the distal end 54 against the rotation tube 32 to enable the distal end 54 to be coupled to the rotation tube 32. In one example, the distal end 54 can be welded to the rotation tube 32, however, it should be noted that other methods and techniques could be employed to couple the coupling post 38 to the rotation tube 32, such as riveting, mechanical fasteners, adhesives, etc.

With particular regard to FIGS. 2 and 3, the rotation tube 32 can be coupled between the handle 30 and the attachment system 34. The rotation tube 32 can act as a moment arm to enable the rotation of the vertebral body V. In one example, the rotation tube 32 can be integrally formed with a portion of the attachment system 34, however, it should be understood that the rotation tube 32 and the attachment system 34 could be formed discretely and assembled together via a suitable technique, such as welding, press-fit, mechanical fasteners, etc., if desired. Generally, the rotation tube 32 can be composed of a suitable biocompatible material, such as a biocompatible metal, metal alloy or polymer. In one example, the rotation tube 32 can be composed of a biocompatible metal or metal alloy. The rotation tube 32 can be generally cylindrical, and can include a proximal or first end 56, a distal or second end 58 and a throughbore or lumen 60.

The first end 56 can be coupled to the handle 30. The second end 58 can be coupled to the attachment system 34. With particular reference to FIG. 3, the second end 58 can include a slot 59. The slot 59 can be sized to receive a portion of the attachment system 34, and can include a post 59a. The post 59a can cooperate with a portion of the attachment system 34, as will be discussed. The lumen 60 can extend from the first end 56 to the second end 58. The lumen 60 can provide access for a driver to insert a locking mechanism, such as a plug or set screw 61 (FIG. 1), into the saddle 22 of the bone engaging member 18 to couple the connecting rod 20 to the saddle 22. The lumen 60 can also enable a driver to engage the rod reduction instrument 12.

Figure 4:
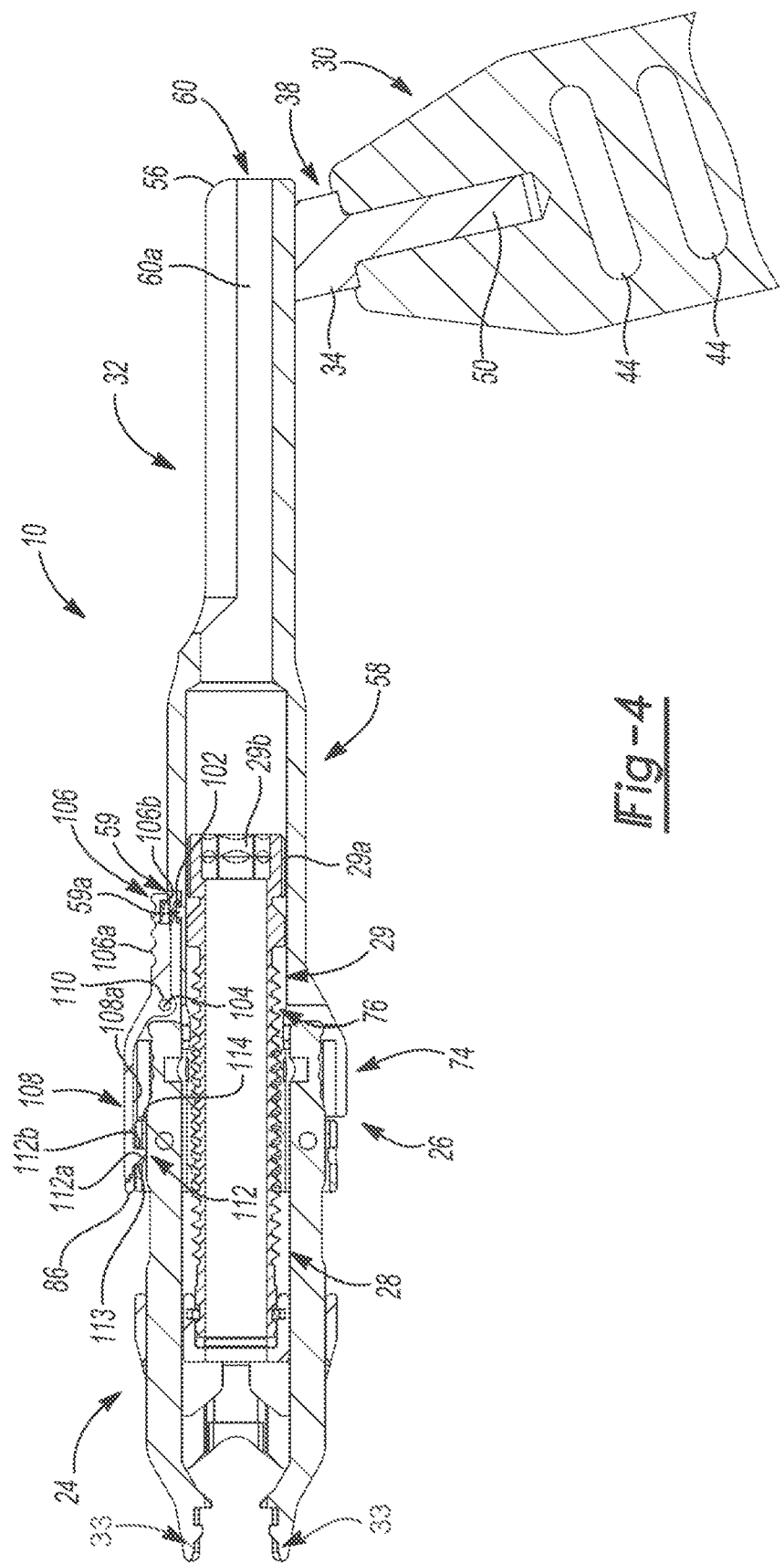
FIG. 4 is a cross-sectional view of the exemplary rotation instrument and rod reduction instrument of FIG. 1, taken along line 4-4 of FIG. 2.

In one example, as particularly shown in FIGS. 3 and 4, the reducing mechanism 28 of the rod reduction instrument 12 may include a rotatable member 29 coupled to a pusher 31. The rotatable member 29 can include a head 29a having a drive feature 29b. In one example, the drive feature 29b can comprise a hexagonal drive feature. The rotatable member 29 is rotatably coupled to the proximal end 26 and rotationally coupled to the pusher 31.

The distal end 24 of the rod reduction instrument 12 includes a pair of jaws 33 for engaging the saddle 22. The jaws 33 are fixedly interconnected with the proximal end 26 of the rod reduction instrument 12. The lumen 60 can enable a driver (see FIG. 11) to engage the drive feature 29b to actuate the reducing mechanism 28 to move the pusher 31 of the rod reduction instrument 12 relative to the distal end 24 of the rod reduction instrument 12 to reduce the connecting rod 20 into the saddle 22.

As will be discussed in greater detail herein, the rotation instrument 10 can enable the rotation of the vertebral body V at any time prior to, simultaneously or after the reduction of the connecting rod 20. A portion 60a of the lumen 60 at the first end 56 can be open to facilitate the insertion of the driver into the lumen 60. It should be noted, however, that the lumen 60 need not include the open portion 60a, and further, if desired, the open portion 60a could extend from the first end 56 to the second end 58.

With particular reference to FIG. 2, the attachment system 34 can be coupled to the second end 58 of the rotation tube 32. The attachment system 34 can releasably couple the rotation instrument 10 to the rod reduction instrument 12. The attachment system 34 can include a mating portion 62 and a coupling system 64. Generally, the attachment system 34 can be composed of a suitable biocompatible material, such as a biocompatible metal, metal alloy or polymer. In one example, the mating portion 62 can be composed of a biocompatible metal or metal alloy, and can be integrally formed with the rotation tube 32. It should be noted, however, the mating portion 62 could be discretely formed and coupled to the rotation tube 32 through a suitable technique, such as mechanical fasteners, adhesive, welding, etc. The mating portion 62 can be shaped to constrain the movement of the rotation instrument 10 relative to the rod reduction instrument 12 to a single degree of freedom. In one example, the mating portion 62 can be formed so as to prevent rotation of the rotation instrument 10 relative to the rod reduction instrument 12 about all three rotation axes, and to prevent translation along two axes.

Figure 5:
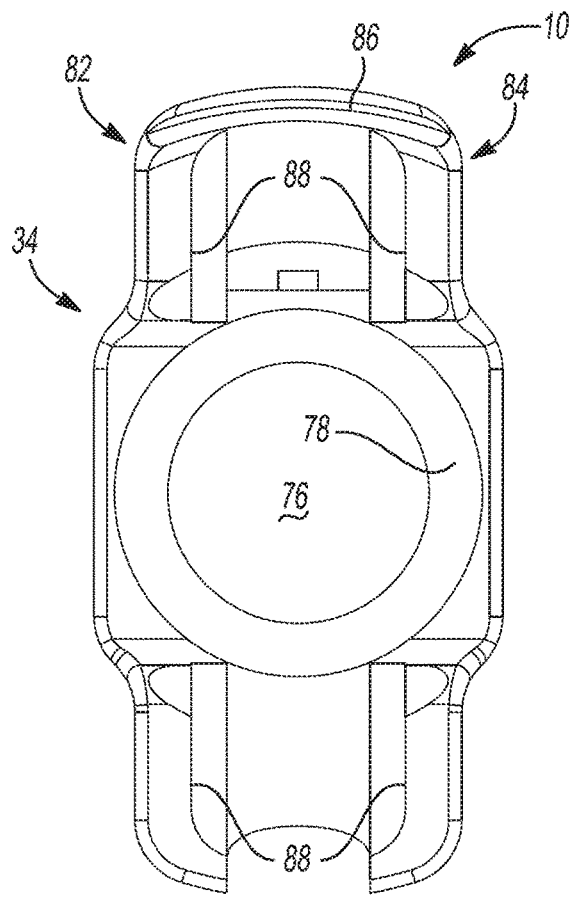
FIG. 5 is an end view of the exemplary rotation instrument of FIG. 2 illustrating an exemplary mating portion of an attachment system for coupling the rotation instrument to the rod reduction instrument.
Figure 6:
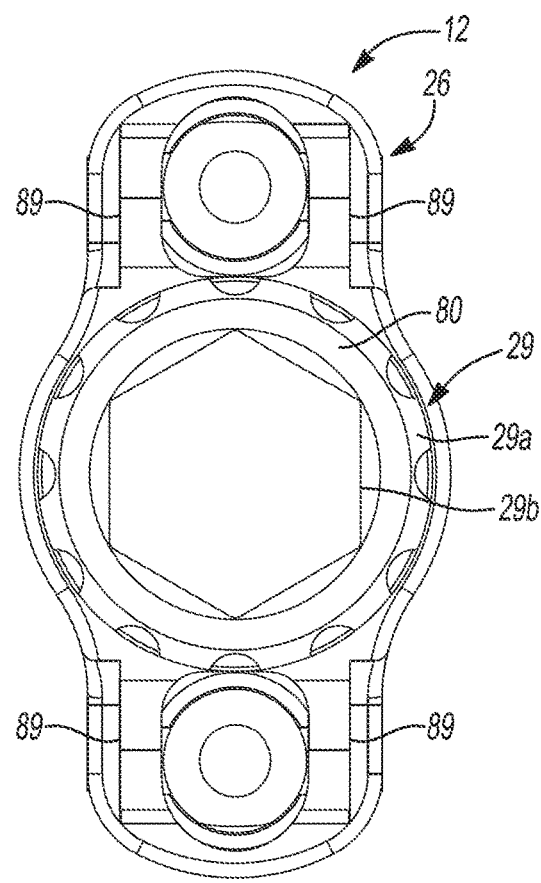
FIG. 6 is an top view of the exemplary rod reduction instrument of FIG. 2.

In this regard, the mating portion 62 can be shaped so that the rotation instrument 10 can slide relative to the proximal end 26 of the rod reduction instrument 12. Generally, the mating portion 62 can have any shape that corresponds with the proximal end 26 of the rod reduction instrument 12 so that the movement between the rotation instrument 10 and the rod reduction instrument 12 is limited to one degree of freedom. In one example, with reference to FIGS. 3 and 4, the mating portion 62 can include a base 70, a first flange 72 and a second flange 74. The base 70 can be formed at a distalmost end of the lumen 60. The base 70 can include a bore 76. The bore 76 can be in communication with the lumen 60 to enable a portion of the reducing mechanism 28 to extend into the lumen 60. The bore 76 can be sized such that the reducing mechanism 28 can move relative to the bore 76. With reference to FIGS. 5 and 6, a distalmost end of the bore 76 can include a counterbore portion 78 (FIG. 5). The counterbore portion 78 can be sized to cooperate with a raised cylindrical lip 80 formed on at the proximal end 26 of the rod reduction instrument 12 (FIG. 6) to constrain the motion of the rotation instrument 10 relative to the rod reduction instrument 12.

With regard to FIG. 3, the first flange 72 and second flange 74 can be generally opposed from each other about the base 70. The first flange 72 can include a first arm 82 and a second arm 84. The first arm 82 can be separated by a distance from the second arm 84 so that a portion of the coupling system 64 can be positioned between the first arm 82 and second arm 84. The first arm 82 and second arm 84 can be coupled together via a member 86 at a distalmost end 82a, 84a of the first arm 82 and second arm 84, respectively. A bore 85 can be formed through a proximal end 82b, 84b of the first arm 82 and second arm 84. The bore 85 can receive a portion of the coupling system 64, as will be discussed in greater detail herein.

With reference to FIGS. 5 and 6, in one example, each of the first arm 82 and the second arm 84 can include a flat surface 88 (FIG. 5). The flat surfaces 88 can be substantially L-shaped, and can cooperate with corresponding flat surfaces 89 formed on the proximal end 26 of the rod reduction instrument 12 (FIG. 6) to constrain the motion of the rotation instrument 10 relative to the rod reduction instrument 12. It should be noted that the flat surfaces 88 are merely exemplary, as the surfaces of the first arm 82 and second arm 84 can have any suitable shape to correspond to the shape of the proximal end 26 of the rod reduction instrument 12.

With reference to FIG. 3, the second flange 74 can include a first arm 90 and a second arm 92. With regard to FIGS. 5 and 6, the first arm 90 and the second arm 92 can each include the flat surface 88 (FIG. 5). The flat surfaces 88 of the first arm 90 and second arm 92 can cooperate with corresponding flat surfaces 89 formed on the proximal end 26 of the rod reduction instrument 12 (FIG. 6) to constrain the motion of the rotation instrument 10 relative to the rod reduction instrument 12. It should be noted that the flat surfaces 88 are merely exemplary, as the surfaces of the first arm 90 and second arm 92 can have any suitable shape to correspond to the shape of the proximal end 26 of the rod reduction instrument 12.

Referring to FIG. 3, the coupling system 64 can enable the rotation instrument 10 to be releasably coupled to the rod reduction instrument 12. The coupling system 64 can be composed of a suitable biocompatible material, such as a biocompatible metal, metal alloy or polymer. The coupling system 64 can include a lever 100, a biasing member or spring 102 and a pivot pin 104. It should be noted that although the coupling system 64 is illustrated and described herein as being separate and discrete from the mating portion 62, the coupling system 64 could be integrally formed with the mating portion 62. Further, although the lever 100, spring 102 and pivot pin 104 are illustrated and described herein as being discrete components, one or more of the lever 100, spring 102 and pivot pin 104 can be integrally formed, if desired. The lever 100 can be movable from a first, latched position to a second, unlatched position by the operator to enable the rotation instrument 10 to be released or decoupled from the rod reduction instrument 12. The lever 100 can include a manipulable portion 106, a latching portion 108 and a pivot bore 110.

A portion of the manipulable portion 106 can be received within the slot 59 of the second end 58 of the rotation tube 32. The manipulable portion 106 can provide a surface for the operator to contact to move the lever 100 from the first position to the second position. In one example, the manipulable portion 106 can include one or more raised surfaces 106a to facilitate contact by the operator. With reference to FIG. 4, the manipulable portion 106 can also include a recess 106b opposite the raised surfaces 106a. The recess 106b can receive a portion of the spring 102 to couple the spring 102 to the lever 100.

The latching portion 108 can be movable between and relative to the first arm 82 and second arm 84 of the first flange 72 of the attachment system 34. The latching portion 108 can include a lip 112. With continued reference to FIG. 4, the lip 112 can extend outwardly from a surface 108a of the latching portion 108. In one example, the lip 112 can be received within a detent 113 defined on the proximal end 26 of the rod reduction instrument 12 to couple the rotation instrument 10 to the rod reduction instrument 12. The lip 112 can include a ramp surface 112a and a flat surface 112b. The ramp surface 112a can contact a ramp surface 114 of the reducing mechanism 28 to move the lever 100 so that the lever 100 can latch onto a portion of the rod reduction instrument 12. This can enable the rotation instrument 10 to be coupled to the rod reduction instrument 12 by moving or sliding the rotation instrument 10 onto the rod reduction instrument 12. The flat surface 112b can cooperate with the detent 113 to retain the rotation instrument 10 on the rod reduction instrument 12 once the rotation instrument 10 is coupled to the rod reduction instrument 12. It should be noted that the latching portion 108 described herein is merely exemplary as the lever 100 could be configured so that the lever 100 can be manually manipulated or pivoted to couple the rotation instrument 10 to the rod reduction instrument 12.

The pivot bore 110 can be defined between the manipulable portion 106 and the latching portion 108. The pivot bore 110 can receive the pivot pin 104 to enable the lever 100 to pivot between the first, latched position and the second, unlatched position. It should be noted that the position of the pivot bore 110 is merely exemplary, as the pivot bore 110 could be positioned at any suitable location. For example, the pivot bore 110 can be located behind the manipulable portion 106 so that the manipulable portion 106 can be pulled to move the lever 100 between the first, latched position and second, unlatched position.

The spring 102 can provide a force to retain the lever 100 in the first, latched position. Generally, one end of the spring 102 can be positioned about the post 59a of the rotation tube 32 and the other end can be received within the recess 106b of the manipulable portion 106 (FIG. 4). The lever 100 can be pivoted against the force of the spring 102 to move the lever 100 from the first, latched position to the second, unlatched position. The pivot pin 104 can be received within the bore 85 of the attachment system 34 to pivotably couple the lever 100 to the attachment system 34 (FIG. 3).

According to one exemplary method, with reference to FIG. 3, in order to assemble the rotation instrument 10, the distal end 54 of the coupling post 38 can be welded to the rotation tube 32. Then, the proximal end 50 of the coupling post 38 can be heated and inserted into the bore 48 of the handle 30 to couple the handle 30 to the coupling post 38. With reference to FIG. 4, the spring 102 can be coupled about the post 59a, and the lever 100 can be positioned over the second end 58 so that the other end of the spring 102 is received within the recess 106b. The pivot pin 104 can then be inserted through the bore 85 and pivot bore 110 to pivotably couple the lever 100 to the attachment system 34.

In order to employ the rotation instrument 10, with reference back to FIG. 1, the first fixation system 14 and the second fixation system 16 can be coupled to the anatomy via any suitable technique. Briefly, it should be noted that the insertion of the first fixation system 14 and the second fixation system 16 into the anatomy is beyond the scope of the present teachings and need not be described herein. In a conventional manner insofar as the present teachings are concerned, exemplary systems and methods for the insertion of the first fixation system 14 and the second fixation system 16 into the anatomy can include those employed in the POLARIS™ Deformity System, POLARIS™ 5.5 or 6.35 Spinal System, or ARRAY® Spinal System, commercially available from Biomet, Inc. of Warsaw, Ind., or the tools disclosed in commonly owned U.S. Patent Publication No. 2008/0077138, filed on Apr. 20, 2007 and U.S. patent application Ser. No. 13/103,069, filed on May 8, 2011, each of which are incorporated by reference herein. In addition, the first fixation system 14 and the second fixation system 16 need not include all of the components illustrated in FIG. 1, but rather, the bone engaging members 18 could comprise a saddle with threads that engages the anatomy, hooks, etc.

Once the bone engaging members 18 of the first fixation system 14 and the second fixation system 16 are coupled to the desired portion of the anatomy, the rod reduction instrument 12 can be coupled to the saddle 22 of the bone engaging member 18. Then, the rotation instrument 10 can be coupled to the rod reduction instrument 12. Note that the connecting rod 20 need not be reduced into the saddle 22 prior to coupling the rotation instrument 10 to the rod reduction instrument 12, and further, the connecting rod 20 need not be inserted into the anatomy prior to coupling the rotation instrument 10 to the rod reduction instrument 12.

In order to couple the rotation instrument 10 to the rod reduction instrument 12, with reference to FIG. 4, the rotation instrument 10 can be moved or slid onto the proximal end of the rod reduction instrument 12 until the ramp surface 112a of the lip 112 of the lever 100 contacts the ramp surface 114 of the rod reduction instrument 12. Once the ramp surface 112a contacts the ramp surface 114, the continued movement of the rotation instrument 10 can overcome the force of the spring 102 to pivot the lever 100 from the first, latched position to the second, unlatched position. The rotation instrument 10 can be advanced onto the rod reduction instrument 12 until the lip 112 latches into the detent 113 of the proximal end 26 of the rod reduction instrument 12. The contact between the flat surface 112b of the lip 112 and the detent 113 can prevent the rotation instrument 10 from being decoupled from the rod reduction instrument 12.

With the rotation instrument 10 coupled to the rod reduction instrument 12, the rotation instrument 10 can be used to rotate one or more vertebral bodies V to correct an axial, coronal or sagittal deformity of the spinal column S. Exemplary techniques for rotating one or more vertebral bodies V to correct a deformity of the spinal column S can be described in U.S. Pat. No. 7,776,072, previously incorporated by reference herein. As the method for using the rotation instrument 10 can be generally known, the method will not be discussed in great detail herein. Briefly, however, with reference to FIG. 1, in order to rotate one or more vertebral bodies V, rotation instruments can be positioned in pairs at the desired location along the anatomy. The rotation instrument 10 can be paired with another rotation instrument 10, or could be paired with any suitable rotation instrument, such as those described herein, or those commercially available from Biomet, Inc. of Warsaw, Ind. In the example of FIG. 1, the rotation instruments 10 can be arranged in pairs and can be connected laterally by a comb 120. The comb 120 can rest on pins 52 inserted through the slots 44 in the handles 30 of the rotation instruments 10. The comb 120 can assist in distributing the forces across the vertebral body V.

In addition, rotation instruments, such as the rotation instrument 10 or those commercially available from Biomet, Inc. of Warsaw, Ind., can be coupled to rod reduction instruments 12 that are coupled to adjacent bone engaging members 18, as shown. In the example of FIG. 1, rotation instruments 10 can be coupled to adjacent vertebral bodies V. These rotation instruments 10 can be coupled together so as to move as a unit or en bloc, by inserting the pin 52 through a desired slot 44 of the handle 30.

With the rotation instruments 10 coupled to the rod reduction instruments 12 and coupled together via the comb 120 and the pins 52, the vertebral bodies V can be rotated with or without the connecting rod 20 being reduced within the saddle 22 of the bone engaging member 18. By allowing the vertebral bodies V to be rotated prior to reducing the connecting rod 20 into the bone engaging member 18, the surgical procedure may be performed more efficiently. In order to reduce the connecting rod 20 into the saddle 22 with the rotation instrument 10 coupled to the rod reduction instrument 12, a driver can be inserted through the lumen 60 and coupled to the drive feature 29*b* (FIG. 4). The driver can be rotated within the lumen 60 to drive the reducing mechanism 28 to reduce the connecting rod 20 into the saddle 22.

Once the desired correction is achieved, the rotation instrument 10 can be decoupled from the rod reduction instrument 12. In order to decouple the rotation instrument 10 from the rod reduction instrument 12, with reference to FIG. 4, the manipulable portion 106 can be pivoted towards the rotation tube 32 against the force of the spring 102. The pivoting of the lever 100 can disengage the lip 112 from the detent 113, thereby allowing the rotation instrument 10 to be moved or slid off of the proximal end 26 of the rod reduction instrument 12.

With reference now to FIGS. 7-10, in one example, a rotation instrument 200 can be employed with the rod reduction instrument 12 to achieve correction of the spinal column S. As the rotation instrument 200 can be similar to the rotation instrument 10 described with reference to FIGS. 1-6, only the differences between the rotation instrument 10 and the rotation instrument 200 will be discussed in great detail herein, and the same reference numerals will be used to denote the same or similar components. The rotation instrument 200 can include the graspable portion or handle 30, a rotation tube 202 and an attachment system 204.

The rotation tube 202 can be coupled between the handle 30 and the attachment system 204. The rotation tube 202 can act as a moment arm to enable the rotation of the vertebral body V. In one example, the rotation tube 202 can be integrally formed with a portion of the attachment system 204, however, it should be understood that the rotation tube 202 and the attachment system 204 could be formed discretely and assembled together via a suitable technique, such as welding, press-fit, mechanical fasteners, etc., if desired. Generally, the rotation tube 202 can be composed of a suitable biocompatible material, such as a biocompatible metal, metal alloy or polymer. In one example, the rotation tube 202 can be composed of a biocompatible metal or metal alloy. The rotation tube 202 can be generally cylindrical, and can include the proximal or first end 56, a distal or second end 208 and a throughbore or lumen 210.

Figure 8:
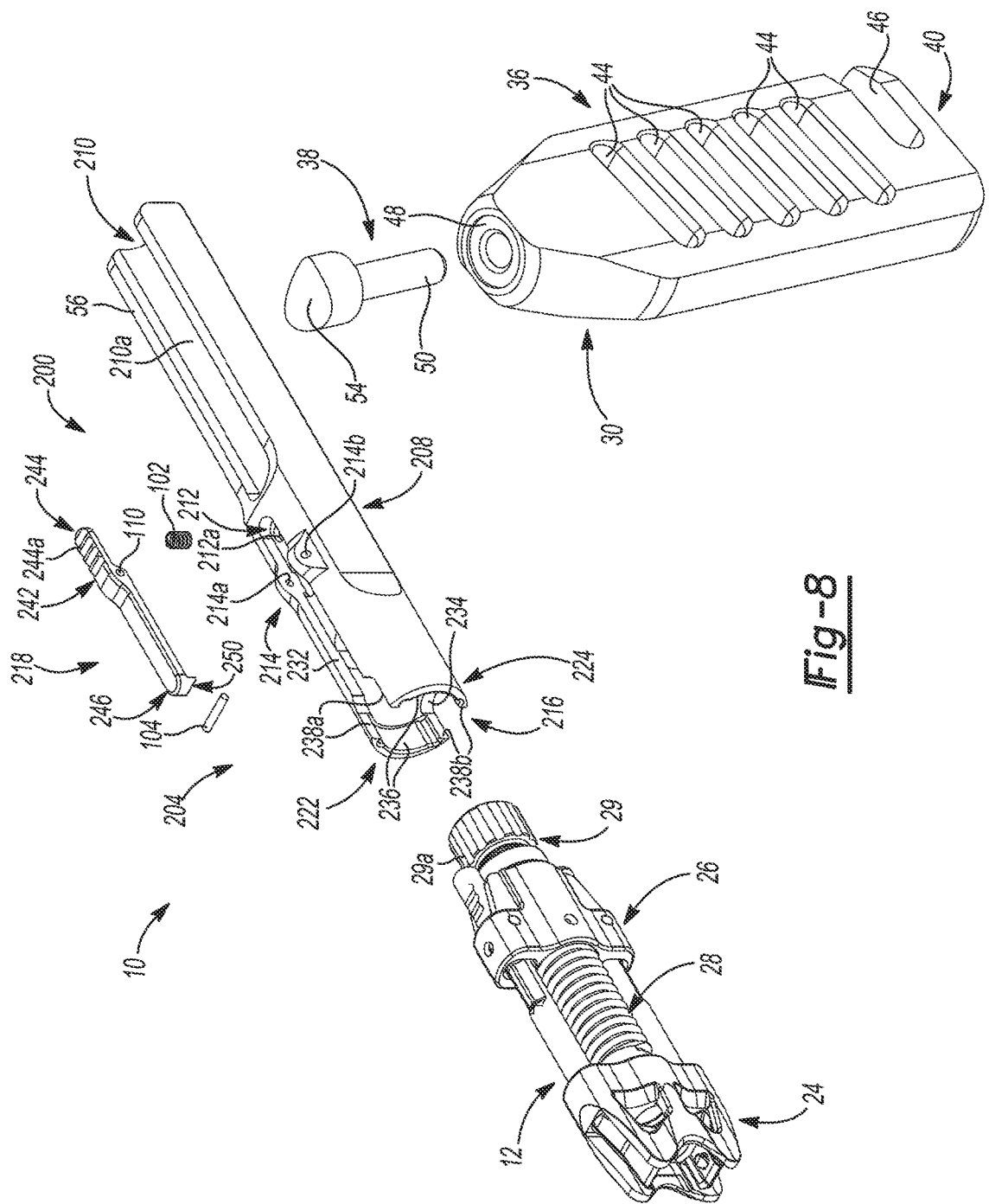
FIG. 8 is an exploded view of the exemplary rotation instrument and rod reduction instrument of FIG. 7.

The second end 208 can be coupled to the attachment system 204. With reference to FIG. 8, the second end 208 can include a slot 212 and at least one bore 214. The slot 212 can be sized to receive a portion of the attachment system 204, and can include a recess 212*a*. The recess 212*a* can receive a portion of the attachment system 204, as will be discussed further herein. The at least one bore 214 can comprise two bores 214*a*, 214*b*, which can be formed on opposite sides of the slot 212. The bores 214*a*, 214*b* can receive a portion of the attachment system 204, as will be discussed further herein.

The lumen 210 can extend from the first end 56 to the second end 208. The lumen 210 can provide access for a driver to insert a locking mechanism, such as the plug 61 (FIG. 1), into the saddle 22 of the bone engaging member 18 to couple the connecting rod 20 to the saddle 22. A portion 210*a* of the lumen 210 at the first end 56 can be open to facilitate the insertion of the driver and plug 61 into the lumen 210. It should be noted, however, that the lumen 210 need not include the open portion 210*a*, and further, if desired, the open portion 210*a* could extend from the first end 56 to the second end 208.

Figure 7:
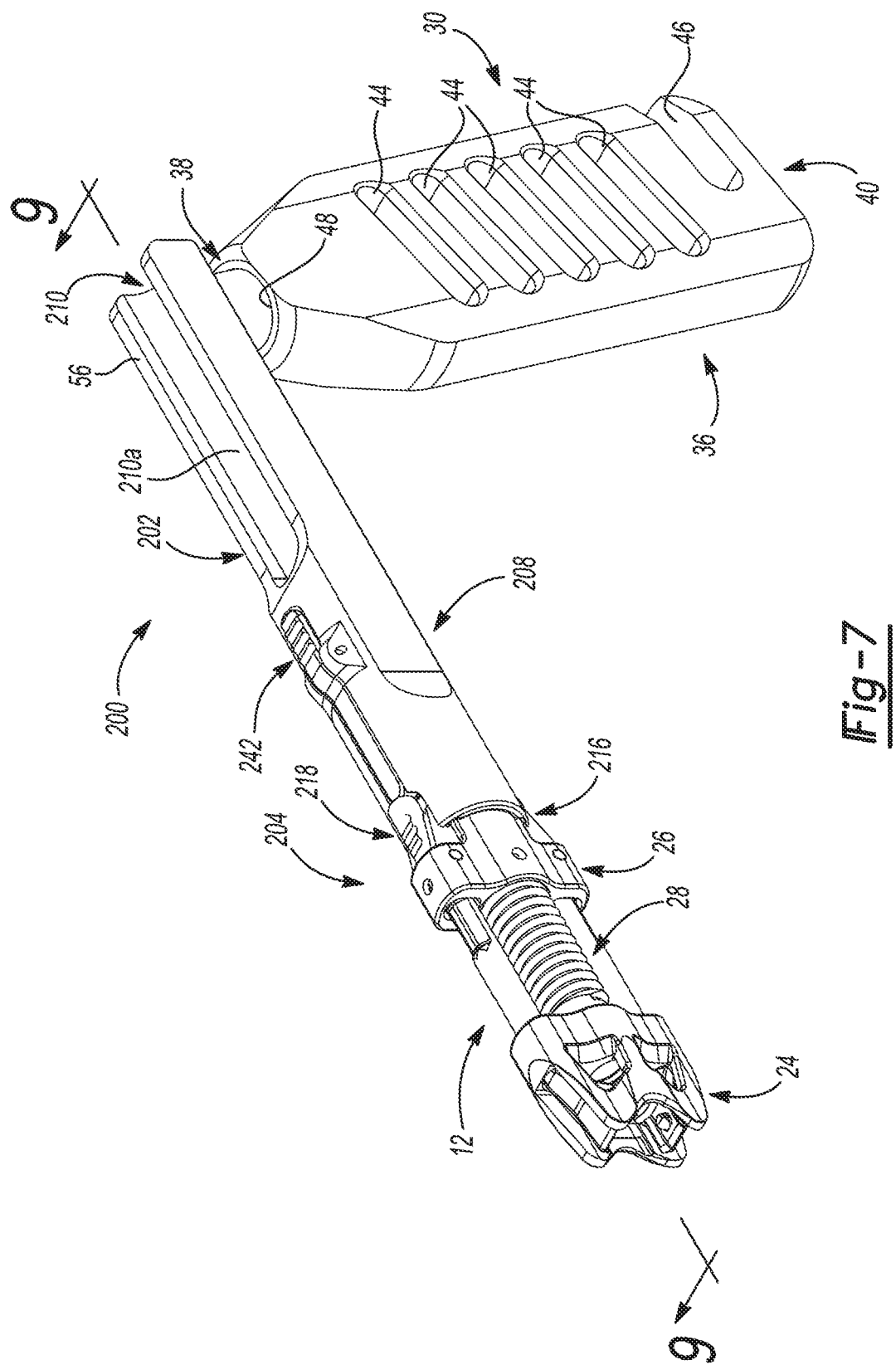
FIG. 7 is a perspective illustration of another assembly including an exemplary rotation instrument coupled to the rod reduction instrument for use in a surgical procedure according to the present teachings.

With reference to FIGS. 7 and 8, the attachment system 204 can be coupled to the second end 208 of the rotation tube 202. The attachment system 204 can releasably couple the rotation instrument 200 to the rod reduction instrument 12. The attachment system 204 can include a mating portion 216 and a coupling system 218. Generally, the attachment system 204 can be composed of a suitable biocompatible material, such as a biocompatible metal, metal alloy or polymer. In one example, the mating portion 216 can be composed of a biocompatible metal or metal alloy, and can be integrally formed with the rotation tube 202. It should be noted, however, that the mating portion 216 could be discretely formed and coupled to the rotation tube 202 through a suitable technique, such as mechanical fasteners, adhesive, welding, etc. The mating portion 216 can be shaped to constrain the movement of the rotation instrument 200 relative to the rod reduction instrument 12 to a single degree of freedom.

In this regard, the mating portion 216 can be shaped so that the rotation instrument 200 can slide relative to the proximal end 26 or reducing mechanism 28 of the rod reduction instrument 12. Generally, the mating portion 216 can have any shape that corresponds with the proximal end 26 of the rod reduction instrument 12 so that the movement between the rotation instrument 200 and the rod reduction instrument 12 is limited to one degree of freedom. In this regard, the mating portion 216 can be formed so as to prevent rotation of the rotation instrument 200 relative to the rod reduction instrument 12 about all three rotation axes, and to prevent translation along two axes. Generally, the rotation instrument 200 can be constrained to one degree of freedom when coupled to the rod reduction instrument 12 after the connecting rod 20 has been reduced to the saddle 22.

Figure 9:
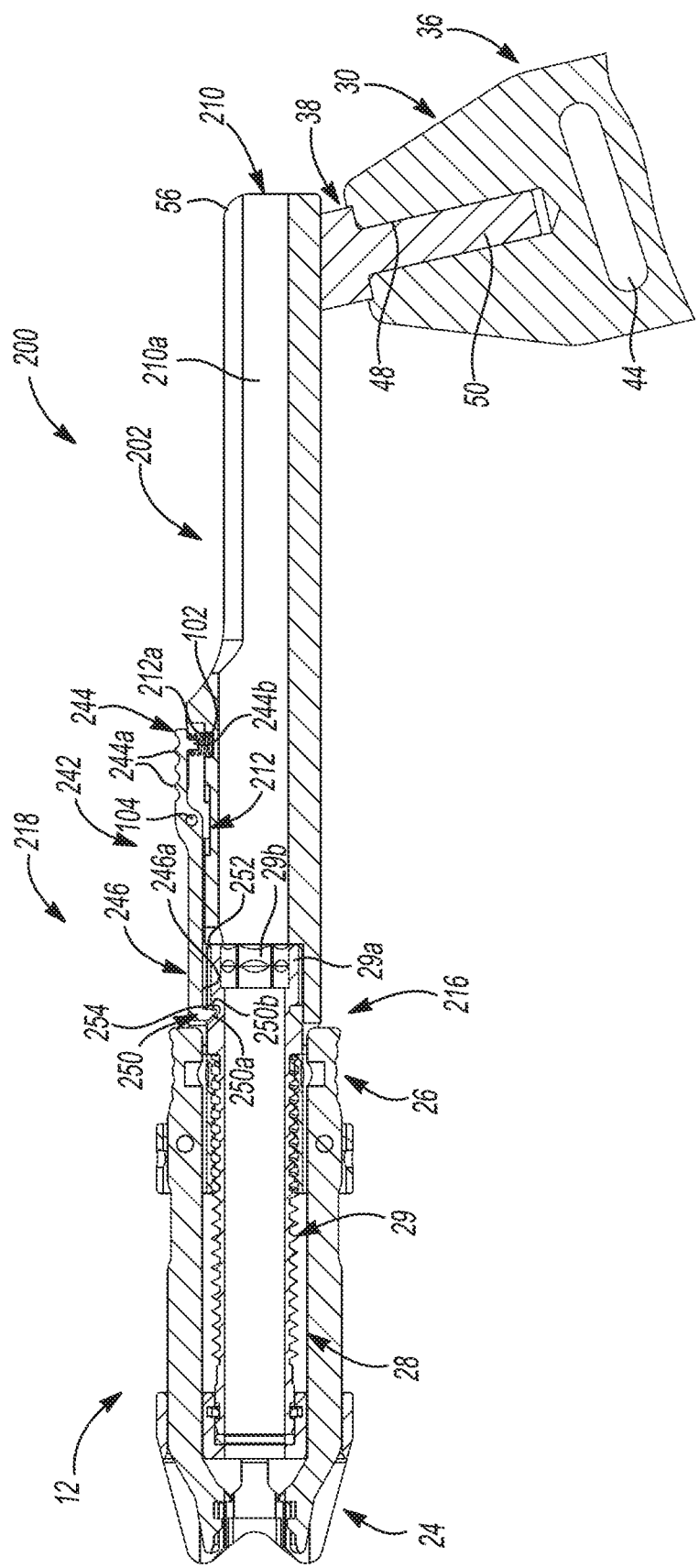
FIG. 9 is a cross-sectional view of the exemplary rotation instrument and rod reduction instrument of FIG. 7, taken along line 9-9 of FIG. 7.

In one example, with reference to FIG. 8, the mating portion 216 can include a first flange 222 and a second flange 224 formed about the lumen 210. The first flange 222 and second flange 224 can each extend from the rotation tube 202, and can be generally opposed from each other about the rotation tube 202. The first flange 222 can be separated from the second flange 224 by a first slot 232 and a second slot 234. The first slot 232 can be longer than the second slot 234, and can receive a portion of the coupling system 218. The second slot 234 can be shaped and sized to correspond to a portion of the proximal end 26 of the rod reduction instrument 12. Generally, the second slot 234 can be sized to enable the first flange 222 and second flange 224 to fit around the head 29*a* of the rotatable member 29 of the reducing mechanism 28 so that the head 29*a* can be received within the lumen 210 (FIG. 9).

Figure 10:
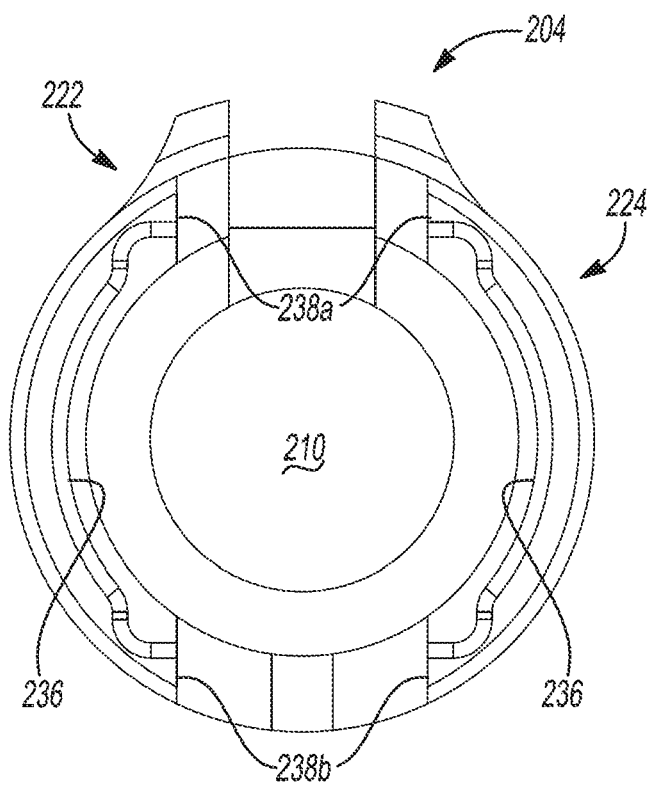
FIG. 10 is an end view of the exemplary rotation instrument of FIG. 7 illustrating an exemplary mating portion of an attachment system for coupling the rotation instrument to the rod reduction instrument.

With reference to FIGS. 8 and 10, the first flange 222 and the second flange 224 can each include a curved portion 236 and at least one flat surface 238. The curved portion 236 can be shaped and configured to fit about the head 29*a* of the rotatable member 29 to constrain the relative motion between the rod reduction instrument 12 and rotation instrument 200. The at least one flat surface 238 can comprise two flat surfaces 238*a*, 238*b*, which can cooperate with flat surfaces 89 formed on the rod reduction instrument 12 (FIG. 6) to constrain the motion between the rod reduction instrument 12 and the rotation instrument 200.

With reference to FIG. 8, the coupling system 218 can enable the rotation instrument 200 to be releasably coupled to the rod reduction instrument 12. The coupling system 218 can be composed of a suitable biocompatible material, such as a biocompatible metal, metal alloy or polymer. The coupling system 218 can include a lever 242, the biasing member or spring 102 and the pivot pin 104. The lever 242 can be movable from a first, latched position to a second, unlatched position by the operator to enable the rotation instrument 200 to be released or decoupled from the rod reduction instrument 12. The lever 242 can include a manipulable portion 244, a latching portion 246 and the pivot bore 110.

A portion of the manipulable portion 244 can be received within the slot 212 of the second end 208 of the rotation tube 202. The manipulable portion 244 can provide a surface for the operator to contact to move the lever 100 from the first position to the second position. In one example, the manipulable portion 244 can include one or more raised surfaces 244a to facilitate contact by the operator. With regard to FIG. 9, the manipulable portion 244 can also include a post 244b opposite the raised surfaces 244a. The post 244b can receive a portion of the spring 102 to couple the spring 102 to the lever 242.

The latching portion 246 can be movable between the first flange 222 and second flange 224 of the attachment system 204. The latching portion 246 can include a lip 250. With continued reference to FIG. 9, the lip 250 can extend outwardly from a surface 246a of the latching portion 246. In one example, the lip 250 can be sized to fit behind the head 29a of the rotatable member 29 to couple the rotation instrument 10 to the rod reduction instrument 12. The lip 250 can include a ramp surface 250a and a flat surface 250b. The ramp surface 250a can contact a ramp surface 252 formed on the head 29a of the rotatable member 29 to move the lever 242 so that the lever 242 can latch onto a portion of the rod reduction instrument 12. This can enable the rotation instrument 200 to be coupled to the rod reduction instrument 12 by moving or sliding the rotation instrument 200 onto the rod reduction instrument 12. The flat surface 250b can contact a surface 254 of the head 29a to retain the rotation instrument 200 on the rod reduction instrument 12 once the rotation instrument 200 is coupled to the rod reduction instrument 12.

According to one exemplary method, with reference to FIG. 8, in order to assemble the rotation instrument 200, the distal end 54 of the coupling post 38 can be welded to the rotation tube 202. Then, the proximal end 50 of the coupling post 38 can be heated and inserted into the bore 48 of the handle 30 to couple the handle 30 to the coupling post 38. The spring 102 can be positioned in the recess 212a, and the lever 242 can be positioned over the second end 208 so that the other end of the spring 102 is positioned about the post 244b (FIG. 9). The pivot pin 104 can then be inserted through the bores 214a, 214b and pivot bore 110 to pivotably couple the lever 242 to the attachment system 34.

As the use of the rotation instrument 200 in a surgical procedure can be similar to the use of the rotation instrument 10 in a surgical procedure, the use of the rotation instrument 200 will not be discussed in great detail herein. Briefly, however, with the rod reduction instrument 12 coupled to the saddle 22 of the bone engaging member 18, and the connecting rod 20 reduced into the saddle 22, the rotation instrument 200 can be coupled to the rod reduction instrument 12. In order to couple the rotation instrument 200 to the rod reduction instrument 12, the rotation instrument 200 can be moved or slid onto the proximal end 26 of the rod reduction instrument 12 until the ramp surface 250a of the lip 250 of the lever 242 contacts the ramp surface 252 of the rod reduction instrument 12 (FIG. 9). Once the ramp surface 250a contacts the ramp surface 252, the continued movement of the rotation instrument 200 can overcome the force of the spring 102 to pivot the lever 242 from the first, latched position to the second, unlatched position. The rotation instrument 200 can be advanced onto the rod reduction instrument 12 until the lip 250 latches about the head 29a of the rotatable member 29 of the rod reduction instrument 12.

The contact between the flat surface 250b of the lip 250 and the head 29a can prevent the rotation instrument 200 from being decoupled from the rod reduction instrument 12.

It should be noted that the coupling of the rotation instrument 200 to the rod reduction instrument 12 is merely exemplary. For example, the rotation instrument 200 can be coupled to the rod reduction instrument 12 before reducing the connecting rod 20 to the saddle 22. In instances where the rotation instrument 200 is coupled to the rod reduction instrument 12 prior to reducing the connecting rod 20 to the saddle 22, the rotation instrument 200 can be constrained to two degrees of freedom as the mating portion 216 may not be in contact with the flat surfaces 89 of the rod reduction instrument 12. In this regard, the head 29a of the rotatable member 29 of the reducing mechanism 28 can extend above the proximal end 26 of the rod reduction instrument 12 prior to reducing the connecting rod 20 into the saddle 22. The rotation instrument 200 can move or slide relative to the head 29a of the rod reduction instrument 12 so that the lip 250 can latch about the head 29a of the rod reduction instrument 12. The contact between the curved portion 236 and the head 29a can restrict relative movement between the rotation instrument 200 and the head 29a of the rod reduction instrument 12, but may not restrict movement between the rotation instrument 200 and the proximal end 26 of the rod reduction instrument 12. Thus, in this example, the rotation instrument 200 can be constrained to two degrees of freedom when coupled to the rod reduction instrument 12. The contact between the flat surfaces 238a, 238b of the rotation instrument 200 and the flat surfaces 89 of the proximal end 26 can constrain motion between the proximal end 26 of the rod reduction instrument 12 and the rotation instrument 200.

With the rotation instrument 200 coupled to the rod reduction instrument 12, the rotation instrument 200 can be used to rotate one or more vertebral bodies V to correct an axial, coronal or sagittal deformity of the spinal column S. Similar to the rotation instruments 10, the rotation instruments 200 can be arranged in pairs and can be connected laterally by the comb 120 and vertically by one or more pins 52 received through the slots 44 in the handles 30. The rotation instrument 200 can be coupled laterally and vertically to any suitable rotation instrument, such as the rotation instrument 10 or those commercially available from Biomet, Inc. of Warsaw, Ind.

Once the desired correction is achieved, the rotation instrument 200 can be decoupled from the rod reduction instrument 12. In order to decouple the rotation instrument 200 from the rod reduction instrument 12, with regard to FIG. 9, the manipulable portion 244 can be pivoted towards the rotation tube 202 against the force of the spring 102. The pivoting of the lever 242 can disengage the lip 250 from about the head 29a of the rotatable member 29, thereby allowing the rotation instrument 200 to be moved or slid off the proximal end 26 of the rod reduction instrument 12.

Figure 11:
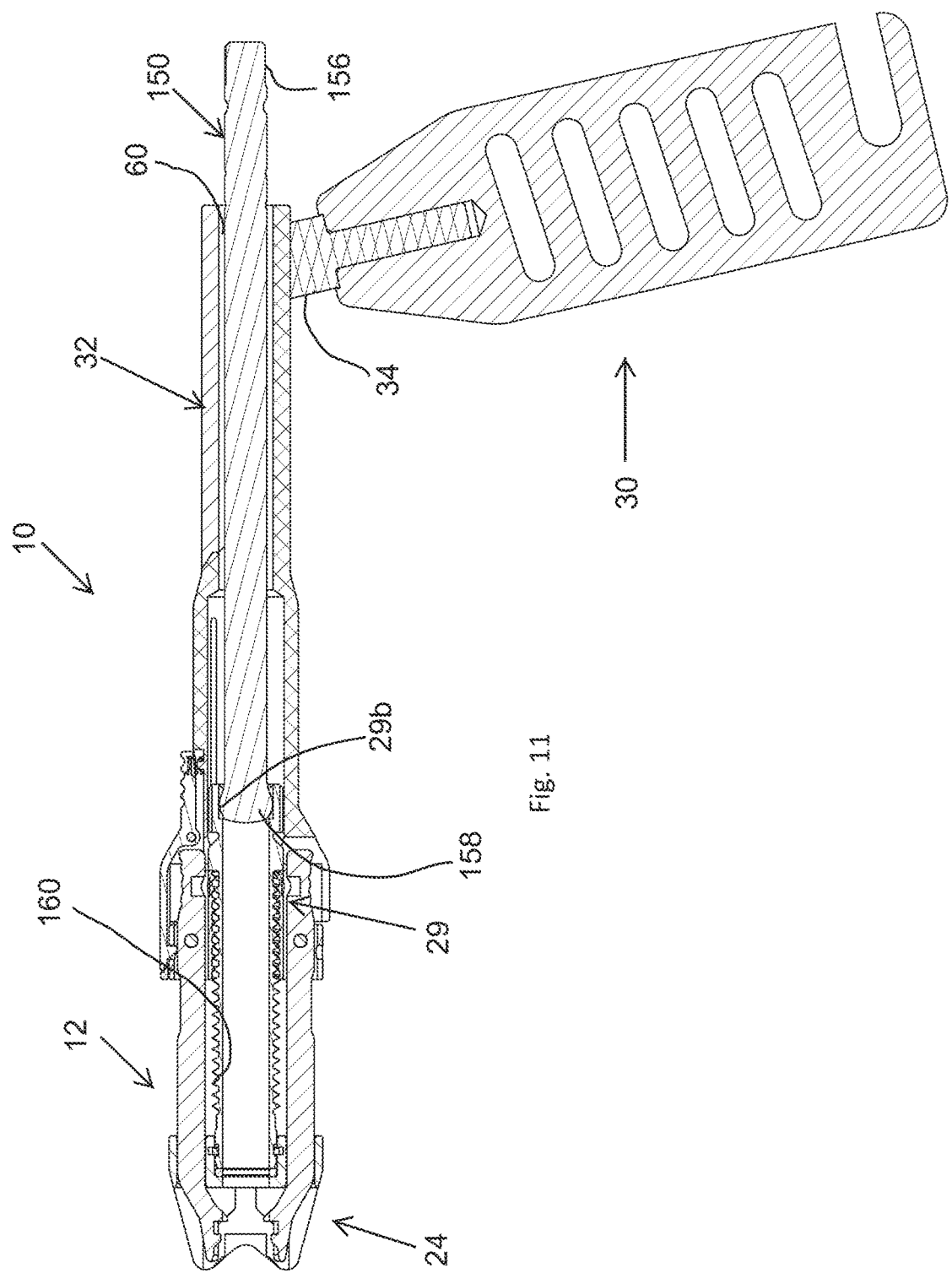
FIG. 11 is a cross-sectional view similar to FIG. 9 illustrating the assembly of the present teachings operatively associated with a quick-connect drive shaft for controlling rod reduction in accordance with the present teachings.
Figure 12:
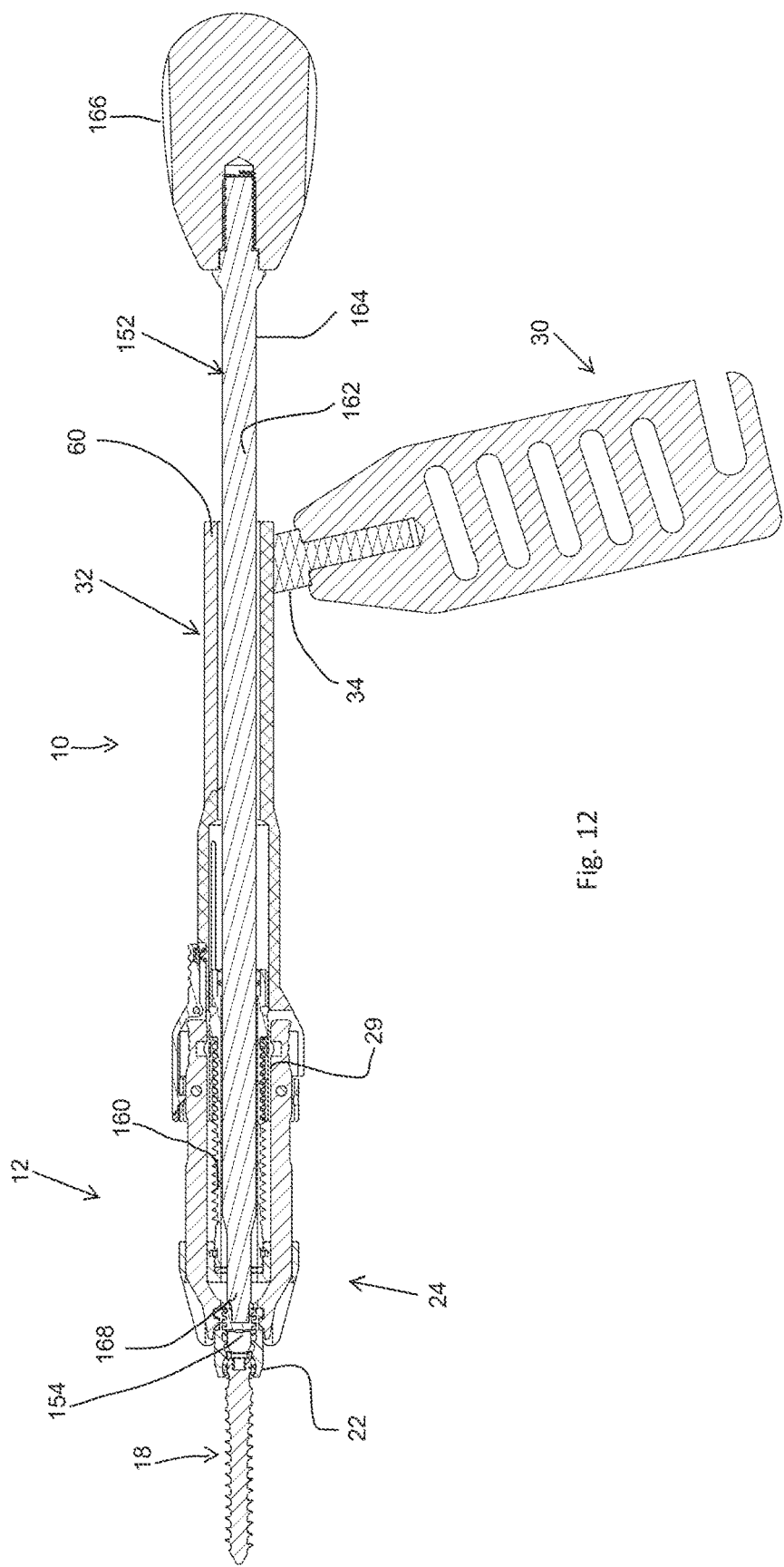
FIG. 12 is a cross-sectional view similar to FIG. 11, illustrating the assembly of the present teachings operatively associated with a plug driver for driving a plug in accordance with the present teachings.

With particular reference to the cross-sectional views of FIGS. 11 and 12, the assembly of FIG. 1 is shown operatively associated with exemplary instruments. In this regard, FIG. 11 shows the assembly operatively associated with a first driver 150 for controlling rod reduction in accordance with the present teachings. FIG. 12 shows the assembly of FIG. 1 operatively associated with a second driver 152 for driving the plug 61.

The first driver is illustrated as a quick-connect drive shaft 150. The drive shaft 150 includes a first end 156 for conventionally coupling to a power driver. A second end 158 non-rotationally engages the drive feature 29b of the rotatable member 29. In the embodiment illustrated, the second end 158 defines a ball hex for engaging the hexagonal drive feature 29b of the screw drive 29. Rotation of the drive shaft 150 operates to control rod reduction in the manner discussed above.

As shown throughout the various views, the rotatable member 29 is cylindrical and defines a throughbore or lumen 160 passing completely therethrough. The lumen 160 may be aligned with the lumen 60. Rotation of the rotatable member 29 distally translates the pusher 31.

The second driver shown in FIG. 12 is illustrated as a plug driver 152. The plug driver includes a shaft 162 operable to pass through the lumen 60 and the lumen 160 of the rotatable member 29. As a first or proximal end 164, the shaft 162 may be coupled to a handle 166. In the embodiment illustrated, the handle 166 may be releasable coupled to the shaft 162 through a threaded connection.

At a second or distal end 168 the shaft 162 is configured to engage the plug 61 of the bone engaging member 18. In this regard, the tip of the shaft 162 may define a hexagonal shaft or other shape that cooperatively engaged corresponding structure of the plug 61 such that the plug 61 rotates with the shaft 152. Rotation of the plug 61 threadably engages the plug 61 with the saddle 22 to secure the rod 20 relative to the saddle 22. Such threaded engagement between the plug 61 and the saddle 22 will be understood to be conventional. In use, the rod 12 can be reduced in the saddle 22 and the plug 61 can be secured to the saddle 22 with a common surgical assembly. This surgical assembly remains secured to the saddle through the jaws 33 throughout this two-step process and thereby facilitates a minimally invasive technique.

It should be noted that the rotation instruments 10, 200 can be available as a kit, which can include any number of components necessary to correct a deformity of the spinal column S. The use of the rotation instruments 10, 200 that can be coupled directly to the rod reduction instrument 12 can improve efficiency during the surgical procedure, which can reduce surgical time. Further, the handles 30 of the rotation instruments 10, 200 can enable the rotation instruments 10, 200 to be used with various other rotation instruments, such as those commercially available from Biomet. Inc. of Warsaw, Ind. In addition, the use of the rotation instrument 10 can provide the surgeon with greater flexibility in performing a surgical procedure as the rotation of the vertebral body V can occur before or after the connecting rod 20 is reduced into the bone engaging member 18 and does not require the removal of the rod reduction instrument 12 prior to attaching the rotation instrument 10.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

The invention claimed is:

1. An assembly, comprising:
a rod reduction instrument, comprising:
a distal end for engaging a saddle of a fixation member;
a proximal end; and
a reducing device disposed between the distal end and the proximal end, the reducing device including a linearly articulating structure operable to reduce a rod in the saddle; and
a rotation instrument comprising:
a mating portion coupleable to the proximal end of the rod reduction instruments; and
a rotation tube extending proximally from the mating portion,
wherein the mating portion includes a lever movable between a first position to secure the mating portion relative to the proximal end of the rod reduction instrument and a second position to decouple the proximal end of the rod reduction instrument, and a base portion configured to constrain rotation of the rod reduction instrument relative to the rotation instrument.

2. The assembly of claim 1, further comprising a handle coupleable to a distal portion of the rotation tube of the rotation instrument, wherein the handle is configured to transfer force to the rotation instrument when coupled thereto.

3. The assembly of claim 2, wherein the handle comprises a body and a coupling post, the coupling post configured to couple the body of the handle to a channel in the distal portion of the rotation tube of the rotation instrument.

4. The assembly of claim 1, wherein the reducing device comprises a throughbore defined therein, the throughbore providing access for a first drive member to secure a plug to the saddle.

5. The surgical assembly of claim 4, wherein the reducing device comprises a rotatable member defining the throughbore.

6. The surgical assembly of claim 5, wherein the rotatable member is cylindrical.

7. The surgical assembly of claim 5, wherein the rotatable member comprises a proximal end configured to engage a second drive member for rotating the rotatable member.

8. The surgical assembly of claim 7, wherein rotation of the rotatable member distally advances a pusher of the reducing device.

9. The surgical assembly of claim 7, wherein the proximal end of the rotatable member defines a hexagonal drive feature.

10. The surgical assembly of claim 5, further comprising the first drive member, the first drive member comprising a distal end with a diameter smaller than a diameter of the throughbore of the reducing device.

11. The surgical assembly of claim 10, further comprising a second drive member, the second drive member comprising a distal end with a diameter larger than the diameter of the throughbore of the reducing device.

12. The surgical assembly of claim 4, wherein the rotation instrument defines a lumen, the lumen aligned with the throughbore of the reducing device when the lever is coupled to the proximal end of the rod reduction instrument.

13. The surgical assembly of claim 12, wherein the reducing device comprises a rotatable member defining the throughbore.

14. The surgical assembly of claim 13, wherein rotation of the rotatable member distally advances a pusher.

15. The surgical assembly of claim 1, wherein the lever is pivotally coupled to the proximal end of the rod reduction instrument.

16. The surgical assembly of claim 15, wherein the lever comprises a manipulable portion, a latching portion, and a pivot bore disposed therein.

17. The surgical assembly of claim 16, wherein the manipulable portion provides a surface for an operator to move the lever from a first position to a second position.

18. The surgical assembly of claim 16, wherein the latching portion comprises a lip that can be received by an indent on the proximal end of the rod reduction instrument when the lever is in the first position.

19. An assembly, comprising:
a rod reducing instrument configured to reduce a rod into a fixation member, comprising:
a distal end for engaging a saddle of the fixation member;
a proximal end; and
a reducing device disposed between the distal end and the proximal end, the reducing device including a linearly articulating structure operable to reduce a rod in the saddle, the reducing device further comprising a throughbore defined therein, the throughbore providing access for a first drive member to secure a plug to the saddle; and
a rotation instrument comprising a mating portion coupleable to the proximal end of the rod reducing instrument and a rotation tube extending proximally from the mating portion, wherein the mating portion includes a lever biased in a first position via a spring to secure the mating portion relative to the proximal end of the surgical instrument and movable to a second position to decouple the proximal end of the surgical instrument, the mating portion including a base portion configured to constrain the rotation instrument to movement with one-degree of freedom relative to the proximal end of the rod reducing instrument.

20. An surgical instrument comprising:
a rod reducing device comprising:
a distal end for engaging a saddle of a fixation member;
a proximal end including a rotatable member; and
a reducing device disposed between the distal end and the proximal end, the reducing device operable to reduce a rod in the saddle upon manipulation of the rotatable member; and
a rotation instrument comprising a mating portion coupleable to the proximal end of the surgical instrument and a rotation tube extending proximally from the mating portion, the mating portion comprising a release lever coupled to the rotation tube via a pivot bore disposed therein, the release lever being movable between a first position to secure the mating portion relative to the proximal end of the surgical instrument via a latching portion that is receivable by the surgical instrument and a second position to decouple the latching portion of the release lever from the surgical instrument, the mating portion shaped such that the rotation instrument is only capable of moving with one-degree of freedom relative to the proximal end of the surgical instrument.

* * * * *

UNITED STATES PATENT AND TRADEMARK OFFICE
CERTIFICATE OF CORRECTION

PATENT NO. : 10,433,884 B2  
APPLICATION NO. : 15/465927  
DATED : October 8, 2019  
INVENTOR(S) : Barrett et al.

Page 1 of 1

It is certified that error appears in the above-identified patent and that said Letters Patent is hereby corrected as shown below:

On page 2, in Column 2, under "Other Publications", Line 29, delete "Oct. 15," and insert --Oct. 16,-- therefor In Column 16, Line 12, in Claim 1, delete "instruments;" and insert --instrument;-- therefor In Column 18, Line 8, in Claim 20, delete "An" and insert --A-- therefor Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*